United States Patent [19]

Warwick et al.

[11] Patent Number: 4,838,263
[45] Date of Patent: Jun. 13, 1989

[54] CHEST COMPRESSION APPARATUS

[75] Inventors: Warren J. Warwick, Minneapolis; Leland G. Hansen, St. Paul, both of Minn.

[73] Assignee: Regents of the University of Minnesota, St. Paul, Minn.

[21] Appl. No.: 45,888

[22] Filed: May 1, 1987

[51] Int. Cl.$^4$ .......................................... A61H 31/00
[52] U.S. Cl. ................... 128/30.2; 128/24 R
[58] Field of Search ...................... 128/30, 30.2, 25 R, 128/39, 40, DIG. 20, 28; 272/130; 60/477

[56] References Cited

U.S. PATENT DOCUMENTS

| | | | |
|---|---|---|---|
| 2,588,192 | 3/1952 | Akerman et al. | 128/30.2 |
| 2,626,601 | 1/1953 | Riley | 128/40 X |
| 2,780,222 | 2/1957 | Polzin et al. | 128/30.2 |
| 2,869,537 | 1/1959 | Jen-chu Chu | 128/30.2 |
| 3,760,801 | 9/1973 | Borgeas | 128/25 R |
| 4,676,232 | 6/1987 | Olsson et al. | 128/28 |

FOREIGN PATENT DOCUMENTS 1247009  7/1986  U.S.S.R. ............................ 128/30.2

Primary Examiner—Richard J. Apley
Assistant Examiner—Howard Flaxman
Attorney, Agent, or Firm—Merchant, Gould, Smith, Edell, Welter & Schmidt

[57] ABSTRACT

Oscillatory chest compression apparatus to aid in loosening and eliminating mucus from the lungs of a cystic fibrosis patient. The apparatus includes a mechanism for applying pressurized air to a bladder covering the chest of a person and a mechanism for venting pressurized air from the bladder. In addition, the apparatus includes a mechanism for supplying the air to the bladder in a regular pattern of pulses. The application of the pressurized pulses and the pulse rate is controllable by the patient.

8 Claims, 2 Drawing Sheets

CHEST COMPRESSION APPARATUS

FIELD OF THE INVENTION

The present invention relates generally to medical devices and, more specifically, to oscillatory chest compression devices which aid in the loosening and elimination of mucus from the lungs of a person, particularly people affected by cystic fibrosis.

BACKGROUND OF THE INVENTION

Cystic fibrosis is a deadly hereditary disease. With one in 20 people carrying the recessive gene, conception of a child having cystic fibrosis results in approximately one in every 400 child-bearing marriages. No cure for the disease has been discovered. Cystic fibrosis affects the mucus secreting glands of the body so that there is an overproduction of mucus. The lungs are continuously filled with the excess mucus, and it must be removed daily to reduce the build-up and the risk of infection. Presently, treatment involves an aerosol therapy three or four times a day to obtain bronchial drainage and a daily physical pounding on the chest wall to loosen mucus for expectoration. Daily treatment can range from four to six hours plus and necessitates a respiratory therapist or at least a trained individual to provide the pummeling of the chest.

The present invention rests on a premise derived from past research with dogs. Oscillating pressure aids mucus clearance in airways and concurrent vibrations decreases the viscosity of the mucus thereby enhancing motility. The research on dogs made use of a modified blood pressure cuff wrapped around the dog in the region of the rib cage. The air bladder in the cuff was pressurized by an oscillating pump.

The art in the area of mechnical vibrations to the body shows such things as inflatable jackets or garments to put on a person to aid in respiration, such as artificial respiration. U.S. Pat. No. 3,043,292, U.S. Pat. No. 2,354,397, U.S. Pat. No. 2,588,192 are representative. Additionally, a garment which provides oscillations for the purpose of messaging the body is shown in U.S. Pat. No. 3,310,050. The art, however, does not address the indicated cystic fibrosis treatment problem.

SUMMARY OF THE INVENTION

The present invention is directed to an oscillatory chest compression apparatus for a person which includes a mechanism for applying a force to the chest of the person. The force applying mechanism includes a bladder for receiving pressurized air. The apparatus also includes a mechanism for supplying a regular pattern of pulses of pressurized air to the bladder, a mechanism for venting the pressurized air from the bladder, and a mechanism for alternately controlling the pulse applying mechanism and the venting mechanism.

In the preferred embodiment, a rotary valve determines the oscillation rate of air entering the bladder from the pressure side and air evacuating the bladder from the depressurizing side. A first blower is used on the pressurizing side of the rotary valve, and a second blower may be used on the evacuation side to rapidly move the air. The bladder is held adjacent to the chest of a person by a shell which is fitted to and fastened about the person. A control switch functions a solenoid valve on the pressurizing side of the rotary valve to stop pressurization during the inspiration portion of the patient's breathing cycle.

In an alternate embodiment, a primary bellows is oscillated to provide air to the bladder adjacent to the chest of the person. In addition, a secondary bellows is oscillated to fill an air reservoir which can rapidly fill the bladder after it has been emptied during an inspiration.

The inventive apparatus is a pioneering solution to the treatment problem faced by people having cystic fibrosis. The advantages of the invention relate to benefits derived from a treatment program utilizing the present apparatus rather than a conventional treatment program. In this regard, a treatment program with the present apparatus provides a cystic fibrosis patient with independence in that the person can operate the machine alone. He/she is no longer required to schedule treatment with a trained individual. This results in increased psychological and physical freedom and self esteem. The person becomes flexible in his/her treatment and can add extra treatments if such would be beneficial as in the case of fighting a common cold. An additional benefit is the vast decrease in cost of treatment.

BRIEF DESCRIPTION OF THE DRAWINGS

The advantages and objectives of the present invention are explained with particularity hereinafter by referring to the drawings briefly described as follows.

DETAILED DESCRIPTION OF THE PREFERRED AND ALTERNATE EMBODIMENTS

Figure 1:
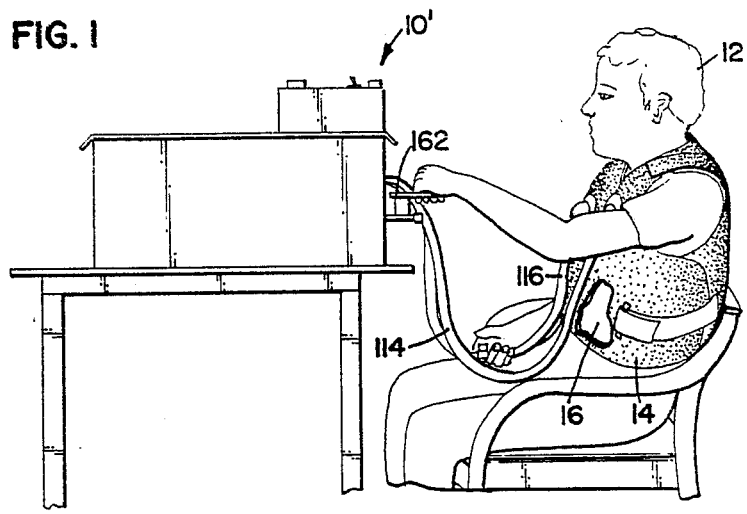
FIG. 1 is an illustration of a person operating the alternate embodiment apparatus in accordance with the present invention.
Figure 2:
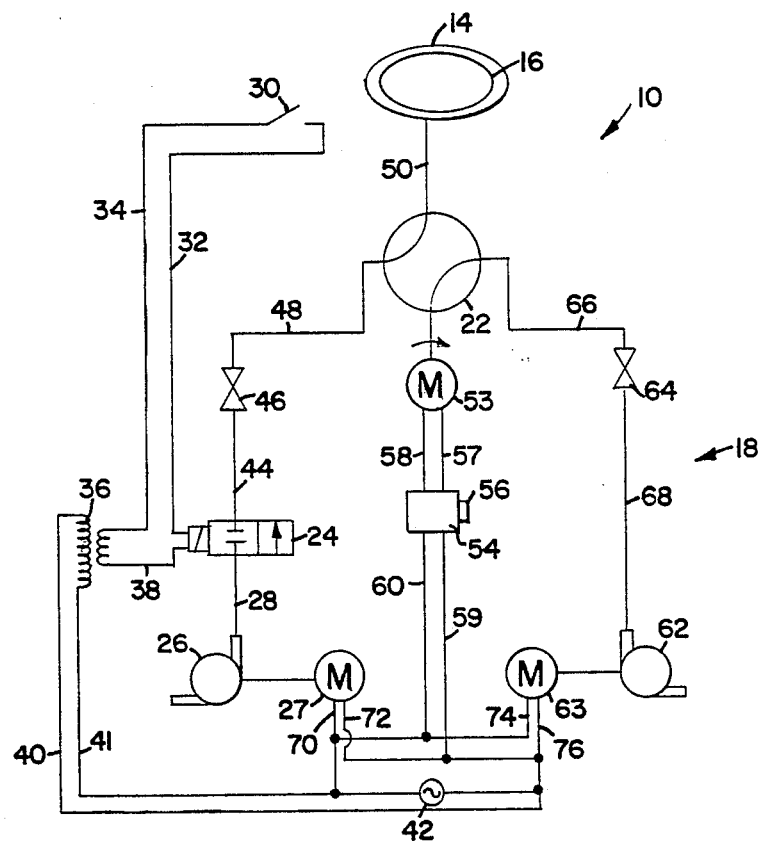
FIG. 2 is a schematic diagram of an apparatus in accordance with the preferred embodiment of the present invention.

Referring then to the drawings wherein like reference numerals designate identical or corresponding parts throughout the several views, and more particularly to FIG. 2, an apparatus in accordance with the present invention is designated generally by the numeral 10. With reference to FIG. 1, an alternate embodiment apparatus is designated generally by the numeral 10'. In FIG. 1, person 12 is shown wearing a shell 14 with an air vest or bladder 16 between the shell and his chest. A hose 114 connects the pulse pumping system 18 with vest bladder 16. Person 12 is shown with his left hand regulating switch 162 which controls the supply of air pulses to vest bladder 16, and with his right hand controlling the venting of vest bladder 16 by opening or closing the end of tube 116.

Preferred embodiment 10 could be illustrated similarly to FIG. 1, except is is controllable with only one hand, as will become apparent. As shown in FIG. 2, the air pulse system 18 of apparatus 10 comprises a pair of high volume regenerative blowers 26 and 62 having output which is controlled by a large bore rotary valve 22. The pressure side blower 26 has been tested using a commercially available unit capable of producing a pressure of 43 inches of water at a volume of 53 cubic feet per minute. Blower 26 is driven by a motor 27. The test unit was driven by a one-half horsepower AC motor at 1725 rpm. The evacuation side blower 62 is driven by a motor 63. The test blower was capable of producing a pressure of 28.5 inches water at a volume capacity of 27 cubic feet per minute. The test blower was operated by a one-eighth horsepower AC motor at 1725 rpm. Preferably, the pressure side blower 26 is oversized relative to the evacuation side blower 62, as indicated with respect to the test units, to accomplish fast reinflation of vest bladder 16 after it has been evacuated.

Alternate positive and negative pressures are applied to vest bladder 16 via a rotary valve 22. During the positive input pulse through valve 22 the negative pressure side of the system is closed. During the negative pressure pulse the positive pressure side of the system is closed. The rotary valve creates alternating positive and negative pressure pulses to vest bladder 16 and is driven by motor 53. During testing, a one-twentieth horsepower DC motor 53 controlled by a conventional DC controller 54 was used. An electronic tachometer with a magnetic pickup was used to monitor valve rotational speed. The blowers operated continuously, so that pulse speed was regulated by controller 54.

A solenoid valve 24 is located between the positive side blower 26 and the rotary valve 22. During testing, solenoid valve 24 has a 1.25 inch bore and was operated by 24 volt power. Valve 24 is normally closed and is controlled by a patient held hand switch 30. In the open position a positive 43 inches of water pressurized air flow is applied to rotary valve 22 which in turn allows the air in the form of a pressure pulse through to vest bladder 16. Since rotary valve 22 opens and closes air flow between positive side blower 26 and vest bladder 16, pulses are created. The pulsing rate is determined by the rotational speed of rotary valve 22 which in turn is determined by motor controller 54.

When solenoid valve 24 is in the closed position, no air flow from the positive side blower 26 passes to vest bladder 16. Rather, vest bladder 16 is evacuated by negative pressure side blower 62. Such evacuation reduces the efforts required by a patient during inhalation. Some patients may find a negative pressure is not needed to evacuate the vest for comfortable inhalation. For such patients, the vacuum or negative pressure blower 62 is optional.

A manual flow valve 46 is located between positive pressure blower 26 and vest bladder 16 to provide adjustment for regulating the flow volume or pulse strength to vest bladder 16. Likewise, a manual flow valve 64 is located between rotary valve 22 and negative side blower 62 to provide control relating to evacuation. That is, for some patients total evacuation of vest bladder 16 may be unnecessary or undesirable. Since rotary valve 22 rotates at a constant speed and since negative side blower 62 operates at a constant speed, when flow valve 64 is set to constrict the flow communication line between rotary valve 22 and blower 62, it will in effect reduce the volume of air which is evacuated during a revolution of rotary valve 22. Therefore, depending on how long the pressure side of apparatus 10 is closed, complete evacuation by the evacuation side may not occur.

With reference to FIG. 2, apparatus 10 is hereinafter described even more particularly. Pressure side blower 26 is in flow communication through hose 28 with normally closed, solenoid valve 24. It is understood that any reference to a hose could as well be a pipe or other mechanism for directing air from one point to another. Solenoid valve 24 is in flow communication with rotary valve 22 through a flow control valve 46, preferably manually operable, wherein hose 44 connects solenoid valve 24 with flow control valve 46 and hose 48 connects flow control valve 46 with rotary valve 22. One or more lines shown as hose 50 connect rotary valve 22 with vest bladder 16. On the negative pressure side, rotary valve 22 is in flow communication through flow control valve 64 with evacuation fan 62. Hose 66 connects rotary valve 22 with flow control valve 64, while hose 68 connects valve 64 with fan 62.

AC motor 27 drives pressurizing fan 26 and is connected via electrical lines 70 and 72 to electrical power source 42. AC motor 63 drives evacuation fan 62 and is connected via lines 74 and 76 to power source 42. DC motor 53 is connected via lines 57 and 58 with controller 54. Controller 54 includes a manual control 56 for varying speed of motor 53. Motor controller 54 receives power via lines 59 and 60 from source 42.

Solenoid valve 24 is connected through an isolation transformer 36 to power source 42. More particularly, solenoid valve 24 is connected to one side of transformer 36 via line 38 and to the other side of transformer 36 via lines 32 and 34 through patient control switch 30. The other side of transformer 36 is connected to power source 42 via lines 40 and 41.

A cystic fibrosis patient is generally weak and has a weak cough and cannot clear mucus from his/her lungs, sometimes hardly at all. A high frequency vibration aids in decreasing the viscosity of the mucus, freeing it from lung walls and thus making it much more likely that a weak cough will be able to clear mucus. As some mucus is cleared, the cough will likely strengthen thereby allowing more and more mucus to be cleared.

Figure 4:
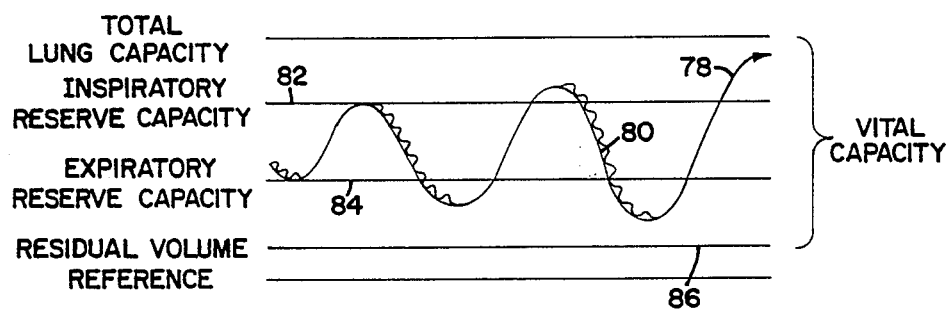
FIG. 4 is an illustration of pressure pulses superimposed on an oscillatory curve representing a patient's breathing cycle.

A more graphic representation is shown in FIG. 4. The lower frequency line 78 represents the breathing cycle of the patient. The higher frequency line superimposed on portions of the low frequency line represents the pulsing motion administered by vest bladder 16 to the patient's chest.

Initially, the patient breathes rather shallow and uses only a small percentage of his/her total lung capacity as represented by the region between the inspiratory reserve capacity line 82 and the expiratory reserve capacity line 84. As some mucus clears, the patient begins using a greater percentage of his/her lung capacity. A treatment goal is to get the patient breathing so deeply that he/she reduces his/her residual volume as represented by line 86, thereby increasing his/her vital capacity.

To use apparatus 10, first a vest bladder 16 and a shell 14 are custom made for the particular patient 12. The vest bladder 16 must cover the region of the chest which covers the lungs. The vest bladder has a single air chamber with at least one and preferably two air ports located near the upper portion of the chest. The vest, on a test model, was made of 15 mil polyurethane with hook and loop closures in front.

Shell 14 may be any one of several possible types. For example, the hard shell may be made from a polypropylene body cast to have split sides to allow for an easy fit. On the other hand, shell 14 may be made as a soft vest from a non-stretch cloth material. Or, shell 14 may be made of nonstretch cloth material, but made to have front and back panels forming pockets to receive rigid polyproplyene plates. All shell types preferably include hook and loop closures.

After the patient has been fitted with a vest bladder 16 and shell 14 such that vest bladder conforms to the patient's chest snugly, but not tightly, hose 50 is connected thereto. The three motors 27, 53 and 63 are then turned on. Since solenoid valve 24 is normally closed, fan 26, although operating, is not yet pressurizing vest bladder 16. Evacuation fan 62, also now operating, is functioning to evacuate vest bladder 16. The patient then closes switch 30 which opens solenoid valve 24 and allows for pressurization of vest bladder 16 and does so with air pulses at a frequency set by control 56 of motor controller 54. If the volume of air from either the pressure side or the evacuation side of the system is too great or not enough, hand control valves 46 and 64 are appropriately functioned.

With the system operating, the patient must learn to control apparatus 10 in accordance with his/her breathing cycle. That is, switch 30 must be held down during expiration and released during inspiration so as to provide pulsing during expiration and evacuation during inspiration. The effect is shown graphically in FIG. 4 by the smooth line 78 directed toward inspiratory reserve capacity line 82 and the superimposed wavey line 80 on line 78 directed toward expiratory reserve capacity line 84. The high frequency pulse rate appropriate for any particular patient is obtained by empirically measuring either the flow rate or the volume of air breathed by the patient at different frequencies and at different time durations of the treatment with apparatus 10. The present apparatus is particularly advantageous in this regard since the pulsing frequency can be tuned to a particular patient to optimize energy transmission to the lungs. Typically, the breathing cycle is a relatively low frequency and for a healthy person is commonly about 0.2 to 0.4 hertz. For a person having cystic fibrosis or other sickness, the breathing frequency may range up to one or two hertz. The high frequency pulsing is generally tuned between 10 to 30 hertz and could go as high as the 30 hertz rate for a small child. In any case, the low frequency breathing cycle will be below 5 hertz, while the high frequency pulsing cycle will be above 5 hertz.

It is noted then that the preferred embodiment apparatus provides a patient a number of advantageous features. Compression pulsing is applied to the entire chest. Pulsing frequency may be tuned for optimal energy transmission. Apparatus 10 is patient controlled. If the patient drops switch 30, apparatus 10 simply evacuates pressure.

An alternate embodiment of apparatus 10 is depicted in FIG. 1, as indicated. Apparatus 10' is shown schematically in FIG. 3. The pulse pumping system comprises a pair of bellows 88 and 90 which may be air ride springs of a type commonly used for suspension of large vehicles. Bellows 88 and 90 operate in opposite directions. Bellows 88 and 90 are driven by a one-half horsepower DC electric motor 92 connected by a five millimeter timing belt 112 to a centrally mounted crankshaft 96. The timing belt runs in conjunction with a pair of pulleys 108 and 110. The crankshaft is held in position by bearing pillow blocks 98 and 100. A DC variable speed motor controller 142 is used to regulate motor speed.

The primary bellows 88 is in direct communication with the vest bladder 16 on the patient. Air is compressed in and evacuated out of the vest by the primary bellows at a rate of typically 10 to 30 hertz. The volume of the pulse is calibrated to patient size and is dependent on the length of the pump stroke and the diameter of the bellows.

The secondary bellows 90 provides an additional airflow to vest bladder 16 which allows the patient to regulate vest bladder contact pressure. This has importance since little or no pressure is needed or in fact desired while the chest wall is expanding during inspiration as previously discussed. Therefore, during inspiration air in the vest bladder is vented to atmosphere, and after inspiration a rapid reinstatement of pressure is necessary for effective chest compression before the next breathing cycle begins. The secondary bellows 90 has directional air flow through a series of one way valves to a small air storage tank 130. The pressure of the air storage tank builds to about one psi during patient inspiration, while the air vest bladder 16 vents to atmosphere. The patient regulates the pressure of the vest bladder by covering or uncovering a vent hole on air hose 116 with a finger. When the vent is open, air is vented to atmosphere. When the patient closes the vent hole and also closes switch 162 controlling solenoid valve 132, the compressed air in the air tank is dumped into the inflatable vest bladder. Such action provides quick reinflation of the vest after the patient has finished inhaling to achieve a contact pressure which is efficient for effective oscillatory chest compression.

Figure 3:
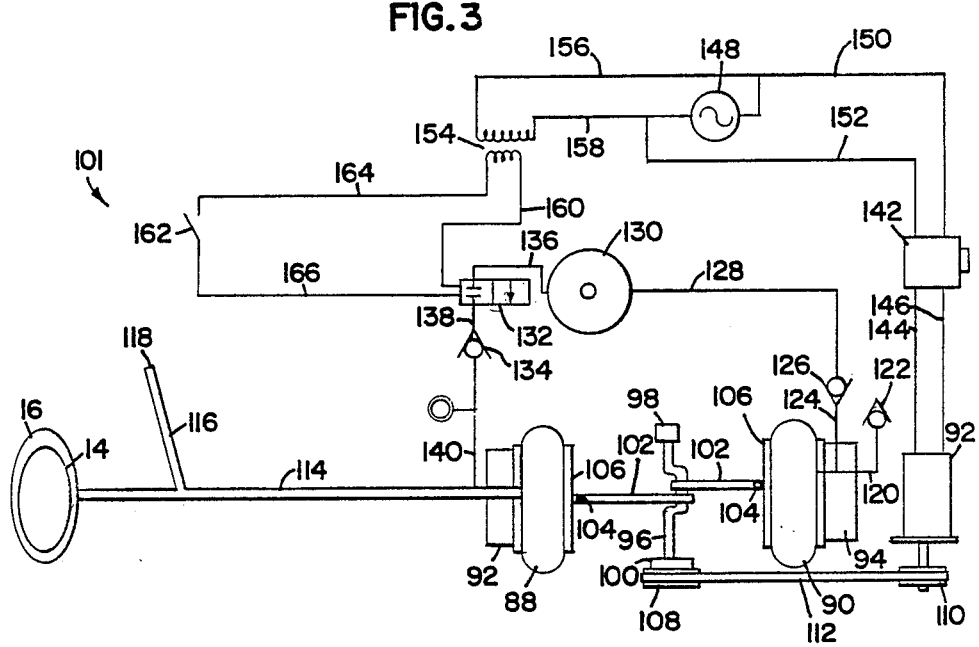
FIG. 3 is a schmatic diagram of an apparatus in accordance with the alternate embodiment illustrated in FIG. 1.

More particularly, apparatus 10' as shown in FIG. 3 includes primary bellows 88 and secondary bellows 90, both of which are driven by DC motor 92. On the sides facing away from one another, both primary and secondary bellows 88 and 90 are held by identical base members 93 and 94. Each base member 93 and 94 presents a flat solid surface against which the bellows 88 and 90 may be compressed. Crank shaft 96 is supported by bearing pillow blocks 98 and 100. Connecting rods 102 are appropriately attached to crank shaft 96 at one end and at an opposite end may be attached through a universal joint 104 to a plunger 106. It is understood that the present description relates only to functional components and that structural framework is necessary and may be easily envisioned and constructed by one skilled in the art. Pulleys 108 and 110 fasten to crank shaft 96 and the shaft of motor 92, respectively, to support timing belt 112.

Primary bellows 88 is in fluid communication through tube 114 with vest bladder 16. Tube 114 includes a branch tube 116 with an open end 118 which the patient closes when he/she wants pressure in vest bladder 16 and opens when he/she wants to vent vest bladder 16. Secondary bellows 90 receives make up air through tube 120 having a one way check valve 122 open in a flow direction leading toward secondary bellows 90. Secondary bellows 90 is also in fluid communication through tube 124 with one way check valve 126 leading in a flow direction away from secondary bellows 90. Valve 126 is in fluid communication through tube 128 with air storage tank 130. Air storage tank 130 is in fluid communication with tube 114 through solenoid valve 132 and one way valve 134 providing flow only in a direction away from storage tank 130, via tubes 136, 138 and 140. When solenoid valve 132 is open, air from storage tank 130 flows to either or both primary bellows 88 and vest bladder 16. In particular, make up air for primary bellows 88 is supplied by vest bladder 16 or storage tank 130.

Motor 92 is electrically connected with controller 142 via lines 144 and 146. Controller 142 is connected to power source 148 via lines 150 and 152. Solenoid valve 132 is isolated from power source 148 by transformer 154. The primary side of transformer 154 is connected to source 148 via lines 156 and 158. The secondary side of transformer 154 is connected to solenoid valve 132 via line 160 and through patient controlled switch 162 via lines 164 and 166.

To use, as with the preferred embodiment firstly the vest bladder and shell 16 and 14 are fitted on patient 12. The patient places one hand at the end of tube 116 and the other hand holds switch 162. Motor 92 is started and regulated to a desired speed in a fashion as described with respect to the preferred embodiment apparatus 10' using motor controller 142. The patient must then learn when to apply compression relative to his/her breathing cycle. That is, during expiration, the patient opens switch 162 and closes end 118 of tube 116. During inspiration, it is generally desirable to vent vest bladder 16 so that the patient then opens switch 162 and opens 118 of tube 116.

Thus, although both the preferred and alternate embodiments of apparatus 10 provide pressure pulses to the chest of a patient and allow the patient controls the rate of the pulses and the application of the pulses, it is apparent that the actual components of the two systems are substantially different. In this regard, it is understood then that even though the advantages and details of structure and function of the preferred and alternate embodiments have been set forth, they are nevertheless exemplary and other equivalents are possible. Therefore, changes made, especially in matters of shape, size and arrangement to the full extent extended by the general meaning of the terms in which the appended claims are expressed, are within the principle of the present invention.

What is claimed is:

1. Oscillatory chest compression apparatus for a person, comprising:
   means for applying a force to the chest of said person, said force applying means including a bladder for receiving pressurized air;
   means for supplying a continuous regular pattern of pulses of said pressurized air to said bladder at a frequency irrespective of and greater than the breathing frequency of said person;
   means for venting said pressurized air from said bladder; and
   means for controlling said pressurized air in said bladder so that the pressure therein can be increased and decreased in correspondence with the expiration and inspiration breathing frequency of said person wherein said force is applied by said applying means at the pulse frequency of said supplying means with greater impact when said controlling means allows increased air pressure in said bladder and with lessor impact when said controlling means allows decreased air pressure in said bladder.

2. Apparatus in accordance with claim 1 wherein said force applying means also includes a shell which said person wears to limit outward expansion of said bladder so that said bladder forces inwardly on said person's chest.

3. Apparatus in accordance with claim 1 wherein said pulse supplying means includes a primary bellows;
   first means for communicating air between said primary bellows and said bladder;
   means for providing air to said primary bellows; and
   primary means for reciprocating said primary bellows between expansion and contraction configurations thereby creating pulses of pressurized air.

4. Apparatus in accordance with claim 3 wherein said air providing means includes:
   a reservoir for pressurized air;
   second means for communicating air in a one-way direction from said reservoir to said primary bellows;
   a secondary bellows;
   third means for communicating air in a one-way direction from said secondary bellows to said reservoir;
   means for inletting air to said secondary bellows; and
   secondary means for reciprocating said secondary bellows between expansion and contraction configurations.

5. Appartus in accordance with claim 1 wherein said venting means includes an outlet port, said controlling means including means operable by said person for covering and uncovering said outlet port.

6. Apparatus in accordance with claim 4 wherein said second communicating means includes a one-way valve and said controlling means includes a stop valve installed in said second communicating means and means operable by said person for functioning said stop valve.

7. Apparatus in accordance with claim 1 wherein said pulse supplying means includes:
   a pressurizing blower providing a first volume rate of air;
   a rotary valve and means for driving said valve;
   first means for communicating the air between said pressurizing blower and said rotary valve; and
   second means for communicating the air between said rotary valve and said bladder; and wherein said venting means includes:
   a depressurizing blower evacuating a second volume rate of air, said second volume rate being less than said first volume rate; and
   third means for communicating air from said rotary valve to said depressurizing blower.

8. Apparatus in accordance with claim 7 wherein said controlling means includes a stop valve installed in said first communicating means, said controlling means further including means operable by said person.

* * * * *